United States Patent
Capote et al.

(10) Patent No.: US 8,029,546 B2
(45) Date of Patent: Oct. 4, 2011

(54) VARIABLE ANGLE OFFSET SPINAL CONNECTOR ASSEMBLY

(75) Inventors: Marco Dagoberto Capote, Memphis, TN (US); Matthew M. Morrison, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1533 days.

(21) Appl. No.: 11/304,318

(22) Filed: Dec. 15, 2005

(65) Prior Publication Data

US 2007/0161987 A1 Jul. 12, 2007

(51) Int. Cl.
*A61F 2/30* (2006.01)
(52) U.S. Cl. ...................................... 606/257
(58) Field of Classification Search .............. 606/54–60, 606/69–73, 246–279, 300–321; 623/17.11–17.16
See application file for complete search history.

(56) References Cited

U.S. PATENT DOCUMENTS

| | | | |
|---|---|---|---|
| 5,047,029 A * | 9/1991 | Aebi et al. ................. | 606/264 |
| 5,575,791 A | 11/1996 | Lin | |
| 5,879,351 A | 3/1999 | Viart | |
| 5,938,663 A | 8/1999 | Petreto | |
| 5,947,965 A | 9/1999 | Bryan | |
| 6,179,838 B1 | 1/2001 | Fiz | |
| 6,251,112 B1 * | 6/2001 | Jackson ..................... | 606/916 |
| 6,482,207 B1 * | 11/2002 | Errico ....................... | 606/264 |
| 6,565,569 B1 | 5/2003 | Assaker et al. | |
| 6,569,164 B1 | 5/2003 | Assaker et al. | |
| 6,626,906 B1 * | 9/2003 | Young ....................... | 606/278 |
| 6,749,612 B1 | 6/2004 | Conchy et al. | |
| 6,881,215 B2 | 4/2005 | Assaker et al. | |
| 7,306,602 B2 * | 12/2007 | Bono et al. ................. | 606/292 |
| 7,648,522 B2 * | 1/2010 | David ........................ | 606/266 |
| 7,704,270 B2 * | 4/2010 | De Coninck ............... | 606/264 |
| 7,803,174 B2 * | 9/2010 | Denis et al. ................. | 606/250 |
| 2003/0163133 A1 * | 8/2003 | Altarac et al. ............... | 606/61 |
| 2004/0138661 A1 | 7/2004 | Bailey | |
| 2004/0254574 A1 | 12/2004 | Morrison et al. | |
| 2005/0113835 A1 | 5/2005 | Ashman | |
| 2005/0137594 A1 * | 6/2005 | Doubler et al. ............. | 606/61 |

FOREIGN PATENT DOCUMENTS

| | | |
|---|---|---|
| DE | 92 15 561 U1 | 1/1993 |
| EP | 0 348 581 | 1/1990 |
| EP | 0779796 B1 | 3/1999 |
| EP | 1 417 935 | 5/2004 |
| FR | 2 743 290 | 7/1997 |
| WO | WO 96/02199 | 2/1996 |
| WO | WO 2006/065666 | 6/2006 |

* cited by examiner

*Primary Examiner* — Thomas C Barrett
*Assistant Examiner* — Christopher Beccia

(57) ABSTRACT

Connector assemblies are provided to couple an elongate member extending along the spinal column to a bone engaging implant engaged to the spinal column. The connector assembly includes a coupler having an implant coupling portion and an elongate member coupling portion. The positioning and orientation of the coupler relative to the implant and elongate member can be adjusted to facilitate engagement of the connector assembly between the implant and elongate member.

16 Claims, 4 Drawing Sheets

VARIABLE ANGLE OFFSET SPINAL CONNECTOR ASSEMBLY

BACKGROUND

Spinal implants can be engaged to or along one or more vertebrae of the spinal column for the treatment of various spinal conditions. Fasteners can be provided to secure the implant to a particular location along the spinal column. The implants can be provided to stabilize the spinal column for treatment, either by fixing the spinal column or by permitting at least some motion of the stabilized motion segments.

Multi-axial and uni-axial screws have been employed for securing elongated implants, such as rods or plates, along one or more motion segments of the spinal column. Such fasteners can comprise many components or parts that make placement and manipulation of the fastener and the elongated implant cumbersome during surgery to achieve the desired position relative to the spinal anatomy. Fasteners that facilitate securement of the elongated implant in a desired positioning along the spinal column can enhance spinal stabilization procedures.

SUMMARY

According to one aspect, a connector assembly includes a coupler for securing an elongate member to an implant engaged to the spinal column. The elongate member is offset to one side of and transversely oriented to the implant. The positioning and orientation of the elongate member and the implant can be adjusted relative to the coupler in a first configuration and locked in position in a second configuration.

According to one aspect, an elongate body is provided for clampingly engaging an implant. The elongate member includes a number of fingers at each end thereof that can clampingly engage the implant when the implant is positioned through an aperture of the elongate body.

According to another aspect, a system for stabilizing a bony segment includes an elongate member positionable along the bony segment and an implant engageable to the bony segment in a transverse orientation to the elongate member. The system further includes a connector assembly for connecting the elongate member to the implant. The connector assembly includes a coupler having a connecting portion defining a receptacle for receiving the elongate member and a pair of arms extending from the connecting portion. The pair of arms each defines an elongated slot aligned with the other for receiving a proximal portion of the implant therethrough in the transverse orientation relative to the elongate member. A distance between the elongate member and the implant can be varied by varying a position of the proximal portion of the implant in the slot. The arms include surfaces facing one another in an angular orientation in a first configuration, and the arms are moveable from the first configuration to a second configuration where the facing surfaces are parallel to one another and the connecting portion clampingly secures the elongate member therein.

According to another aspect, a system for stabilizing a bony segment includes an elongate member positionable along the bony segment and an implant engageable to the bony segment in a transverse orientation to the elongate member. The system further includes a connector assembly for connecting the elongate member to the implant. The connector assembly includes a coupler having a connecting portion defining a receptacle for receiving the elongate member and a pair of arms extending from the connecting portion. The pair of arms each defines an elongated slot aligned with one another. A clamp is pivotally received in the receptacle of the connecting portion when the connecting portion is in a first configuration. The elongate member extends through the clamp. A sleeve is positioned about the proximal portion of the implant. The sleeve and the proximal portion are received in the aligned slots of the arms in the transverse orientation to the elongate member. The sleeve includes an outwardly extending portion adjacent a distal end thereof. A ring positioned about the sleeve is in contact with the outwardly extending portion and a distal one of the pair of arms. An engaging member is engaged about the sleeve adjacent a proximal end thereof. The engaging member is threadingly movable along the sleeve to a second configuration where the engaging member contacts a proximal one of the pair of arms to compress the pair of arms against the ring and the ring into contact with the outwardly extending portion of the sleeve to clamp the sleeve about the proximal portion of the implant.

According to another aspect, a method for coupling an elongate member to an implant engageable to a spinal column comprises: providing a coupler having a connecting portion defining a receptacle for receiving the elongate member therethrough and a pair of arms secured to one another with the connecting portion, the pair of arms defining elongated slots aligned with one another and extending transversely to the receptacle; positioning the elongate member through the receptacle of the coupler, the receptacle including a clamp about the elongate member pivotally received in the receptacle; positioning a proximal portion of the implant through the aligned slots, the proximal portion of the implant including a sleeve positioned thereabout; and moving the pair of arms toward one another to clamp the elongate member in the receptacle and to clamp the sleeve to the proximal portion of the implant.

According to another aspect, a surgical implant system includes an elongated body extending between a proximal end and a distal end. The body defines an aperture extending therethrough opening at the distal and proximal ends. The body further includes a number of proximal slots extending therethrough and opening at the proximal end to divide a proximal portion of the body into a number of fingers moveable toward one another into the aperture. The body also includes a number of distal slots extending therethrough along a distal portion of the body and opening at the distal end. The distal slots divide the distal portion into a number of legs moveable toward one another into the aperture. The system also includes an implant, and the body is positionable about the implant and engageable thereto by clamping the proximal fingers and the distal legs to the implant.

These and other aspects will be discussed further below.

DETAILED DESCRIPTION OF THE ILLUSTRATED EMBODIMENTS

Figure 1:
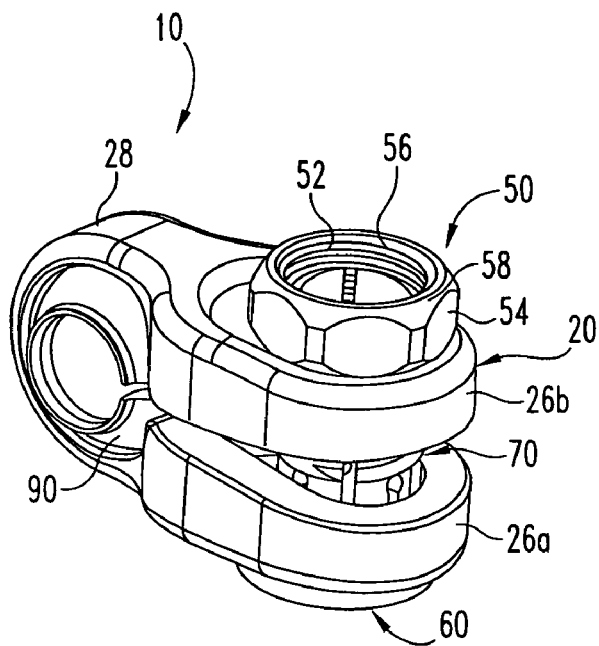
FIG. 1 is a perspective view of a connector assembly.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Figure 2:
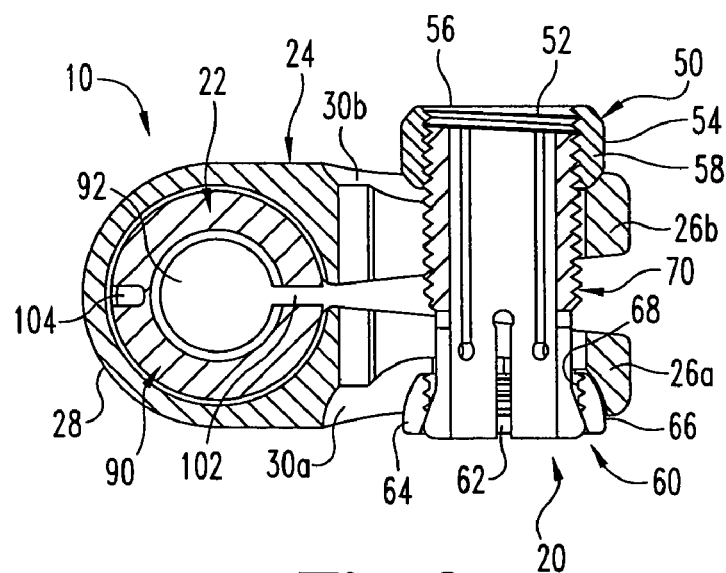
FIG. 2 is a section view of the connector assembly of FIG. 1.
Figure 3:
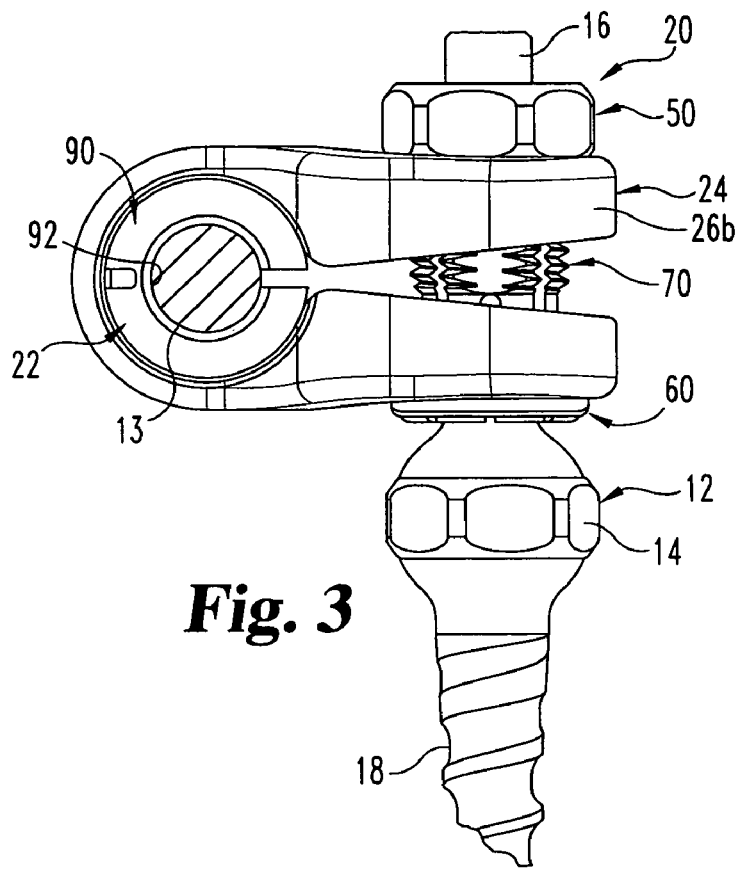
FIG. 3 is an elevation view of the connector assembly of FIG. 1 assembled with an anchor, shown in partial elevation view, and an elongate member, shown in section view.
Figure 4:
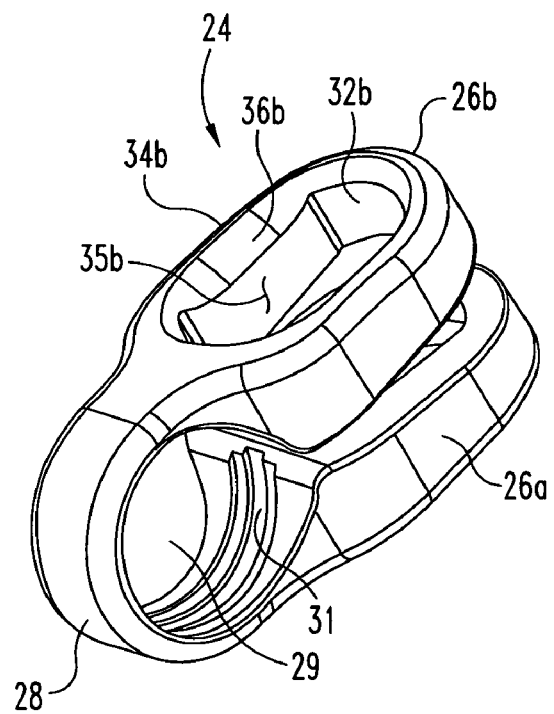
FIG. 4 is a perspective view of a coupler of the connector assembly of FIG. 1.
Figure 5:
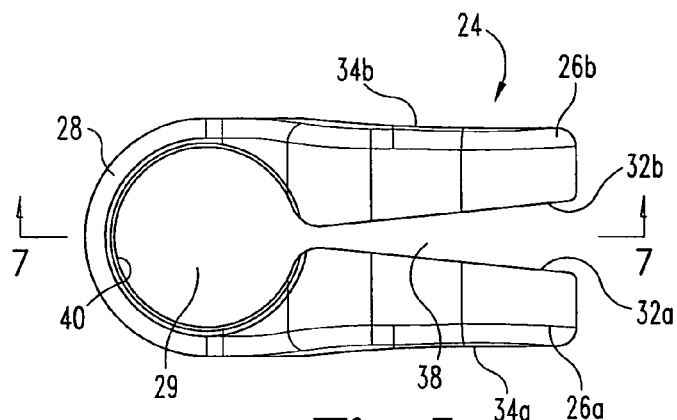
FIG. 5 is an elevation view of the coupler of FIG. 4.
Figure 6:
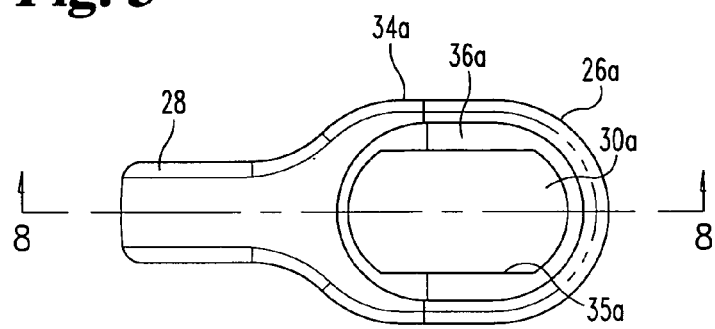
FIG. 6 is a plan view of the coupler of FIG. 4.

FIGS. 1-3 show an embodiment of a connector assembly 10, and in FIG. 3 an implant 12 and elongate member 13 are shown coupled to connector assembly 10. Connector assembly 10 is operable to connect implant 12, such as a bone anchor, with elongate member 13, such as a spinal rod, to form an implant system. Implant 12 can be a bone screw or other suitable anchoring device engageable to bone or another implant. The implant can include a portion for engagement with connector assembly 10. Elongate member 13 can be a spinal rod or other member positionable along the spinal column to maintain or assist in maintaining one or more vertebrae in a desired position.

Connector assembly 10 can include an implant coupling portion 20 extending through a coupler 24 of connector assembly 10. Implant coupling portion 20 can be engaged to a proximal portion 16 of implant 12. In one embodiment, proximal portion 16 can be a post, arm, or other suitable extension or portion for positioning through coupler 24. In a further embodiment, the implant coupling portion 20 can include an elongate body with a number of fingers or legs at each end that can clampingly engage the implant positioned in the elongate body.

Connector assembly 10 can also include an elongate member coupling portion 22 in coupler 24 at a location offset to one side of implant 12. Elongate member 13 can extend through coupler 24 and be engaged thereto with elongate member coupling portion 22 in a transverse orientation to implant 12.

Implant 12 in the illustrated embodiment is a bone screw and can include a distal shaft 18 having a thread profile therealong for engaging bone, and an enlarged head 14 between distal shaft 18 and proximal portion 16. Head 14 can include flats or other tool engaging features therearound to engage a driving tool to facilitate engagement of implant 12 to the underlying bone. Various forms for implant 12 are contemplated, including threaded and non-threaded anchors, uniplanar and multi-axial pivoting arrangements. Bone engaging portions in the form of hooks, clamps, spikes, cables, interbody implants, fusion devices, non-cannulated screws, fenestrated screws, and bolts, are also contemplated, for example. In another form, the implant can be connected to another implant, and/or can be a bone plate, staple, and/or cross-connector extending between spinal rods, for example.

Elongate member 13 can be structured either alone or in combination with one or more other elongate members, implants and/or connector assemblies to provide a desired stabilization effect. In the illustrated embodiment, elongate member 13 is a spinal rod structured to extend between at least two connector assemblies 10 secured to the spinal column with corresponding bone engaging implants. Elongate member 13 can also extend between at least one connector assembly 10 and another implant having any type of suitable connection mechanism to secure elongate member 13 to the implant. Various forms for elongate member 13 are contemplated, including rods, tethers, cables, wires, and plates, for example.

Connector assembly 10 can include coupler 24 having aligned slots 30a, 30b for receiving implant coupling portion 20 and implant 12 therethrough in a first direction. Coupler 24 can further include a receptacle 29 for receiving elongate member coupling portion 22 and elongate member 13 therethrough in a second direction that is transverse to the first direction. Furthermore, coupler 24 is arranged so that elongate member 13 is offset to one side of implant 12.

Coupler 24 is shown in isolation in FIGS. 4-8. Coupler 24 includes a pairs of arms 26, selectively referred to as a distal arm 26a and a proximal arm 26b. Arms 26a, 26b are interconnected by a connecting portion 28 extending therebetween. Connecting portion 28 includes a circular shape to loop between arms 26a, 26b and form receptacle 29. A gap 38 is formed between arms 26a, 26b in their normal, uncompressed state.

Figure 7:
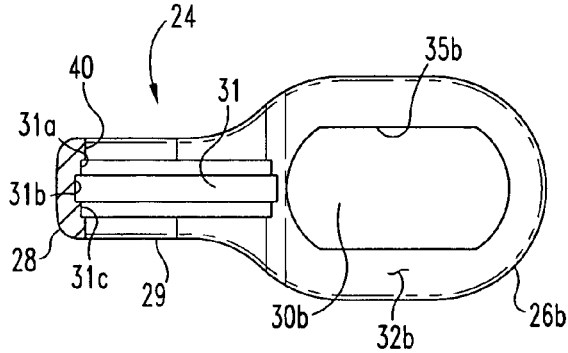
FIG. 7 is a section view through line 7-7 of FIG. 5.
Figure 8:
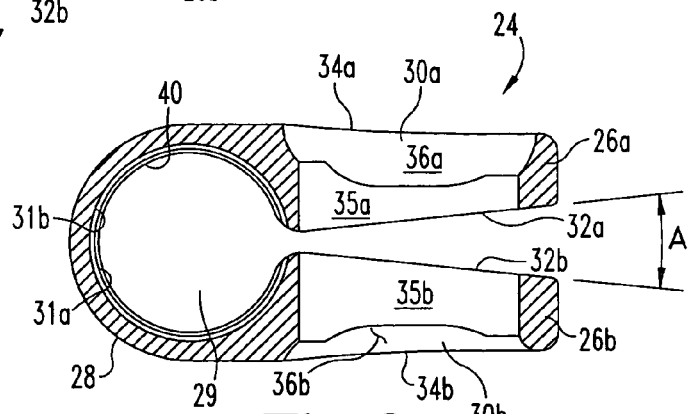
FIG. 8 is a section view through line 8-8 of FIG. 6.

As shown in FIG. 7, connecting portion 28 includes a groove 31 extending about an inner surface 40 thereof that defines receptacle 29. Groove 31 includes outer portions 31a, 31c and middle portion 31b extending into inner surface 40 of connecting arm 28. Middle portion 31b is deeper than outer portions 31a, 31c so that an edge is formed between each of the portions 31a, 31b, 31c and the respective adjacent portion of inner surface 40. These edges can bite into the outer surface of clamp 90 when arms 26a, 26b are compressed toward one another, thereby locking clamp 90 in position in connecting portion 28.

Arms 26a, 26b each include a respective slot 30a, 30b extending therethrough transversely to receptacle 29. Slots 30a, 30b open at a central facing surface 32a, 32b extending along each of the arms 26a, 26b adjacent the other arm 26a, 26b. Slots 30a, 30b each further open toward a respective one of the outer surfaces 34a, 34b along each of the arms 26a, 26b. Slots 30a, 30b each include a vertical wall surface 35a, 35b extending from the respective facing surface 32a, 32b, and a sloped outer wall surface 36a, 36b that transitions from the vertical surfaces 35a, 35b to the respective outer surface 34a, 34b. Sloped surfaces 36a, 36b allow ring 60 and engaging member 50, respectively, to be recessed therein to provide a more low profile arrangement and to center the ring and engaging member between the vertical walls surfaces 35a, 35b of slots 30a, 30b.

Sloped surfaces 36a, 36b and vertical wall surfaces 35a, 35b can provide a somewhat elongated arrangement in the medial-lateral direction and permit adjustability in the location of implant 12 relative to elongate member 13. Furthermore, facing surfaces 32a, 32b can form an angle A relative to one another when connecting portion 28 is in a normal, unflexed condition. Facing surfaces 32a, 32b can diverge in the direction away from receptacle 29 and connecting portion 28.

Connecting portion 28 can flex in response to compression of arms 26a, 26b toward one another to reduce angle A and position facing surfaces 32a, 32b adjacent to or in contact with one another. The normally diverging angular relationship of facing surfaces 32a, 32b away from receptacle 29 allows ends 42a, 42b to contact one another first when arms 26a, 26b are compressed. The entire surface areas of facing surfaces 32a, 32b can be positioned in contact with one another when clamped together. It is further contemplated that only a portion of facing surfaces 32a, 32b contact one another. Connecting portion 28 is also securely and tightly engaged about clamp 90 as arms 26a, 26b are compressed toward one another.

Implant coupling portion 20 includes a sleeve 70 positionable about proximal portion 16 of implant 13 and through the aligned slots 30a, 30b. Implant coupling portion 20 also includes a ring 60 positionable about and adjacent to the distal end of sleeve 70 for positioning in contact with distal arm 26a. An engaging member 50 is positionable about sleeve 70 and moveable therealong to contact proximal arm 26b. Engaging member 50 is movable along sleeve 70 to compress arms 26a, 26b of coupler 24 between engaging member 50 and ring 60, which in turn compresses sleeve 70 about proximal portion 16 of implant 13 to secure connecting assembly 10 thereto.

Elongate member coupling portion 22 includes a clamp 90 positionable about elongate member 13. Clamp 90 is received in receptacle 29 of connecting portion 28 of coupler 24. When coupler 24 is in its first, unflexed configuration, clamp 90 can pivot in receptacle 29 to facilitate orienting coupler 24 to extend between implant 12 and elongate member 13. Connecting portion 28 can be configured so that when coupler 24 is moved to a second, flexed configuration as arms 26a, 26b are moved toward one another, connecting portion 28 compresses clamp 90 to clampingly engage elongate member 13 therein. In addition, connecting portion 28 can include groove 31 with edges that bite into clamp 90 and prevent it from pivoting in receptacle 29.

The arrangement of connector assembly 10 allows the positioning of coupler 24 relative to implant 12 to be adjusted as needed to accommodate the spinal anatomy while maintaining a low profile in the medial-lateral direction and a nearly tangential proximity of the implant 12 and elongate member 13. Medial-lateral adjustability can be provided by the slotted arms 26a, 26b of coupler 24 extending in the medial-lateral direction in the implantation orientation for a posterior surgical stabilization procedure. Furthermore, the orientation of the portion of the implant extending through slots 30a, 30b can be varied at various angles. For example, the arms 26a, 26b can be obliquely angled to the longitudinal axis of the implant. Clamp 90 interfaces with coupler 24 to provide rotational and angular adjustability of coupler 24 about elongate member 13. The arms 26a, 26b can be obliquely angled relative to elongate member 13. A clamping action about elongate member 13 and locking engagement with coupler 24 maintains the positioning of clamp 90 when coupler 24 is secured to implant 12. Furthermore, sleeve 70 can be adjusted in positioning along proximal portion 16 of implant 12, and secured to implant 12 at any one of a number of positions therealong by the clamping action of sleeve 70 about proximal portion 16 as engaging member 50 is secured to clamp arms 26a, 26b against one another and against ring 60.

Figure 11:
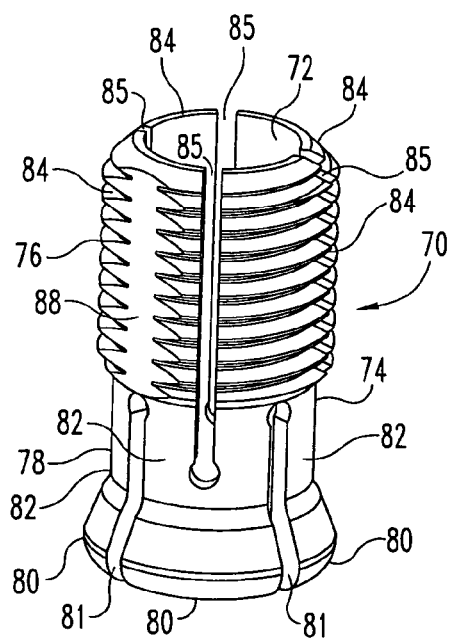
FIG. 11 is a perspective view of a sleeve of the connector assembly of FIG. 1.
Figure 12:
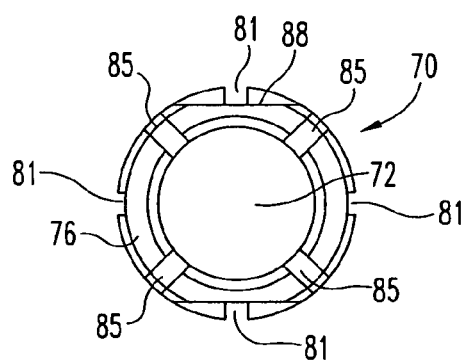
FIG. 12 is a top plan view of the sleeve of FIG. 11.

In the illustrated embodiment, sleeve 70 includes an elongated, cylindrical body 74 having a proximal threaded portion 76 along at least a portion of a length thereof. Sleeve 70 is sized and shaped to fit within and move along slots 30a, 30b. However, it should be appreciated the sleeve 70 can be shaped or configured differently in other embodiments. Sleeve 70 is shown in isolation in FIGS. 11 and 12. Threaded portion 76 includes one or more flat sections 88. In one embodiment, sleeve 70 includes two flat sections 88 positioned substantially diametrically opposite each other along the outside of sleeve 70. An aperture 72 extends axially through sleeve 70.

Proximal slots 85 extend through the wall of sleeve 70 along proximal portion 76 to form a plurality of proximal fingers 84. In the illustrated embodiment, there are four proximal slots 85 and four fingers 84 spaced equally about proximal portion 76. Other numbers of fingers and slots are also contemplated. Proximal fingers 84 can flex relative to one another to permit and facilitate clamping of proximal portion 76 of sleeve 70 about proximal portion 16 of implant 12 when engaging member 50 is secured thereto.

Sleeve 70 includes one or more axial slots 81 extending along a distal portion 78 thereof. Slots 81 also open distally in sleeve 70, forming a respective one of the legs 82 therebetween. In the illustrated embodiment, there are four slots 81 equally positioned about a circumference of sleeve 70 and which extend generally parallel to aperture 72. Other embodiments contemplate other numbers and spacing of slots and legs. Sleeve 70 further includes a foot 80 extending radially outwardly therefrom at the distal end of each of the legs 82. Feet 80 each include a proximally oriented convex surface adjacent a distal end of sleeve 70. The outer cross-sectional dimension of sleeve 70 at feet 80 is larger than an outer cross-sectional dimension of sleeve 70 at other locations along its length.

Ring 60 can be generally annular in form and have a wall 64 defining an outer surface 66. Wall 64 further defines internal threads 68 to allow it to be positioned over the external threads of sleeve 70 in close contact with sleeve 70. As shown in FIG. 2, ring 60 is positioned in abutting engagement with the convexly curved surfaces of feet 80. The inner surface of ring 60 can be concavely curved to provide a concave-convex interface with feet 80. The concave-convex interface can generate a force with a radially inwardly extending component that clamps legs 82 about proximal portion 16.

As also shown in FIG. 2, engaging member 50 includes a wall 58 extending about an internally threaded bore 52. Bore 52 includes internal threads 56 extending therearound, and engaging member 50 includes an outer surface 54 having flats or other suitable tool engaging structure that can be engaged by a tool to facilitate threadingly advancing engaging member 50 along sleeve 70. Engaging member 50 can compress the proximal fingers 84 of sleeve 70 toward aperture 72 to clamp implant 12 therein.

Figure 9:
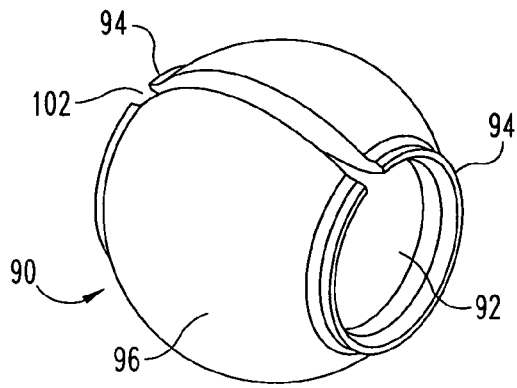
FIG. 9 is a perspective view of a clamp of the connector assembly of FIG. 1.
Figure 10:
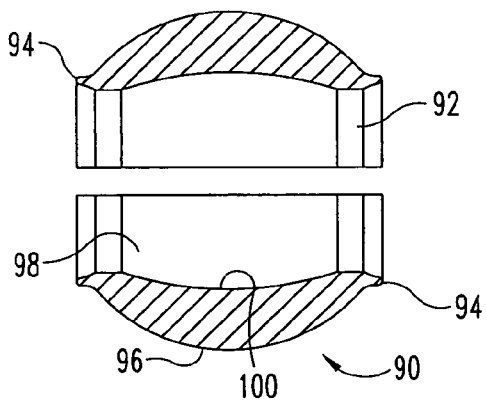
FIG. 10 is a sectional view of the clamp of FIG. 9.

Clamp 90 is shown in isolation in FIGS. 9 and 10, and in receptacle 29 in FIGS. 1-3. Clamp 90 includes a passage 92 extending therethrough to receive elongate member 13. Clamp 90 can include an outer surface 96 that defines a spherical shape between opposite end flanges 94. Clamp 90 further includes an internal wall 98 defining passage 92. Internal wall 98 includes a concave portion 100 that is concavely curved and spaced from a portion of the length of elongate member 13 extending through clamp 90.

Clamp 90 further includes a gap 102 extending axially therealong that allows portions of the clamp 90 to be moved toward one another by reducing gap 102. Such movement can be facilitated by a hinge 104 formed in clamp 90 opposite gap 102. In the illustrated embodiment, hinge 104 is formed by reducing a wall thickness of clamp 90, providing a living or integral hinge. Other embodiments contemplate other structures for clamping about elongate member 13, including shape memory material and material sufficiently deformable without a hinge. The concavely curved portion 100 spaces the inner wall of clamp 90 from elongate member 13, allowing circumferential contact by end flanges 94 with the elongate member 13. This arrangement can reduce binding or twisting that could be created as clamp 90 is clamped about elongate member 13. Other embodiments contemplate that clamp 90 contacts elongate member 13 along the entire or substantially all of the length of passage 92, or that clamp 90 contacts elongate member 13 about a mid-portion of passage 92.

In use, connector assembly 10 can be used in surgical procedures relating to the spine. The surgeon can gain access to a surgical site using any suitable technique, such as through an incision and retraction of tissue, or through minimally invasive access portals or pathways. One or more of the implants 12 can be provided in the form of bone screws can be threadingly implanted into one or more vertebrae, such as in the pedicle in a posterior stabilization procedure. Proximal portion 16 can extend from the pedicle. If not pre-positioned on proximal portion 16, sleeve 70 can be positioned on implant 12. Furthermore, if not already positioned about sleeve 70, ring 60 can be advanced along sleeve 70 to a location adjacent to feet 80.

Coupler 24 can be positioned about clamp 90 with clamp 90 loosely retained in receptacle 29. Elongate member 13 can be positioned through clamp 90. It is contemplated that assembly of coupler 24 with clamp 90 and elongate member 13 can be completed prior to implantation of elongate member 13 or during implantation. In either case, elongate member 13 can be positioned along the spinal column with coupler 24 secured thereto and arms 26a, 26b extending medial-laterally from elongate member 13. Coupler 24 can then be positioned over implant 12 with proximal portion 16 and sleeve 70 extending through slots 30a, 30b. Prior to finally securing coupler 24, the orientation of elongate member 13 relative to coupler 24 can be adjusted by pivoting clamp 90 in connecting portion 28. In addition, the positioning of implant 12 in arms 26a, 26b can be adjusted by moving coupler 24 along the implant in slots 30a, 30b.

Engaging member 50 is positioned about sleeve 70 and threaded distally therealong to contact proximal arm 26b. Further advancement of engaging member 50 along sleeve 70 moves facing surfaces 32a, 32b toward one another and seats distal arm 26a against ring 60. Ring 60 in turn pushes distally on feet 80. The concave-convex interface between ring 60 and feet 80 causes sleeve 70 to flex inwardly about legs 82, and into clamping engagement with proximal portion 16 of implant 12. Engaging member 50 can be further advanced until facing surfaces 32a, 32b are in face-to-face contact with one another and/or extend generally parallel to one another.

In spinal surgical procedures, elongate member 13 and one or more connector assemblies 10 and other implants discussed herein may be employed unilaterally. Alternatively, a second elongate member 13 and one or more connector assemblies 10 and/or other suitable connection mechanism with other implants can be secured to the other side of the vertebral level or levels to be stabilized. Multiple elongate members 13 and corresponding implant/connector assemblies 10 can be secured along the same side of the spinal column in either uni-lateral or bi-lateral stabilization procedures.

In one technique, the underlying bone forms a portion of a vertebral body of the spinal column. The underlying bone can be a part of the anterior, oblique, antero-lateral, lateral or posterior vertebral elements, including the pedicle, spinous process, transverse processes, lamina or facet, for example. Applications in techniques along any portion or portions of the spinal column are contemplated, including the cervical, thoracic, lumbar and sacral regions. The connector assemblies, implants and elongate members can be positioned along the spinal column in invasive procedures where skin and tissue are dissected and retracted to expose the implant locations, or in minimally invasive procedures where one or more of the connector assemblies, elongate members and/or implants are guided through at least the tissue or access portals adjacent the column to the desired implantation location.

Engaging member 50 is engageable about sleeve 70 to secure implant 12 in engagement with coupler 24. Engaging member 50 can include a proximal break-off portion (not shown) that severs upon application of a threshold torque, although embodiments without a break-off portion are contemplated as shown. Sleeve 70 is illustrated as an externally threaded sleeve that engages the internal thread profile along engaging member 50 and ring 60. Other configurations are also contemplated for engagement with engaging member 50 and ring 60, including multiple component members including internally and/or externally threaded portions, frictional engagement, shape memory materials, snap fits, clamps and bayonet-locks, for example.

While the invention has been illustrated and described in detail in the drawings and foregoing description, the same is to be considered as illustrative and not restrictive in character. All changes and modifications that come within the spirit of the invention are desired to be protected.

What is claimed is:

1. A system for stabilizing a bony segment, comprising:
an elongate member positionable along the bony segment;
an implant engageable to the bony segment in a transverse orientation to the elongate member;
a connector assembly for connecting the elongate member to the implant, said connector assembly comprising:
a coupler having a connecting portion defining a receptacle for receiving the elongate member and a pair of arms extending from the connecting portion, said pair of arms each defining an elongated slot aligned with the other for receiving a proximal portion of the implant therethrough in the transverse orientation relative to the elongate member, wherein:
said elongated slot includes a length that extends transversely to the elongate member and transversely to the implant so that a distance between said elongate member and said implant can be varied by varying a position of said proximal portion of said implant along said length of said slot;
said anrms include surfaces facing one another in an angular orientation in a first configuration and said arms are moveable from said first configuration to a second configuration where said facing surfaces are parallel to one another and said connecting portion clampingly secures the elongate member therein;
an implant coupling portion positioned about said proximal portion of said implant, said implant coupling portion including an elongate sleeve having an axially extending aperture for receiving said proximal portion, a ring defining a bore that receives said sleeve with said ring movably positioned in contact with outwardly extending portions of said sleeve adjacent a distal end thereof, and an engaging member engageable about said sleeve along a proximal end of said sleeve, wherein said arms are positioned between said ring and said engaging member and movable from said first configuration to said second configuration as said engaging member is threadingly advanced along said sleeve toward said arms to compress said arms against ring, wherein said sleeve includes:
a number of proximal slots extending axially along a portion of a length thereof from a proximal end of said sleeve, said proximal slots dividing said sleeve into a number of proximal fingers moveable toward one another to grip said proximal portion of said implant therebetween; and
a number of distal slots extending axially along a portion of a length therefrom from a distal end of said sleeve, said distal slots dividing said sleeve into a number of distal legs, said outwardly extending portions forming a foot adjacent a distal end of a respective one of said legs, said legs being moveable toward one another to grip said proximal portion of said implant therebetween;

wherein said engaging member is movable along said sleeve into contact with a proximal one of said arms to move said arms toward one another and compress said arms between said engaging member and said ring, said ring engaging said feet and moving said legs toward one another to grip said proximal portion of said implant as said engaging member and said ring are tightened against said arms.

2. The system of claim 1, wherein said connecting portion includes a clamp in said receptacle about said elongate member, said clamp being pivotal in said connecting portion in said first configuration and being locked in position in said connecting portion in said second configuration.

3. The system of claim 2, wherein said connecting portion include an inner surface defining said receptacle and a groove about said inner surface, said groove including a number of portions defining edges therebetween for biting into said clamp in said second configuration.

4. The system of claim 3, wherein said clamp includes an outer surface defining a spherical shape and an inner passage for receiving said elongate member therethrough, said inner passage including a surface along said elongate member including a portion concavely curved along said elongate member, said concavely curved portion extending between end portions that clampingly engage said elongate member in said second configuration.

5. The system of claim 4, wherein said clamp includes a gap extending along one side thereof in communication with said inner passage and a groove opposite said gap forming a hinge to facilitate clamping of said elongate member therein.

6. A system for stabilizing a bony segment, comprising: an elongate member positionable along the bony segment; an implant engageable to the bony segment in a transverse orientation to the elongate member;

a connector assembly for connecting the elongate member to the implant, said connector assembly comprising:

a coupler having a connecting portion defining a receptacle for receiving the elongate member and a pair of arms extending from the connecting portion, said pair of arms each defining an elongated slot, said slots being aligned with one another;

wherein said pair of arms of said coupler are positioned between said ring and said engaging member and said sleeve includes:

an axially extending aperture for receiving said proximal portion of said implant; a number of proximal slots extending axially along a portion of a length of said sleeve from a proximal end of said sleeve, said proximal slots dividing said sleeve into a number of proximal fingers moveable toward one another to grip said proximal portion of said implant therebetween; and a number of distal slots extending axially along a portion of a length of said sleeve from said distal end of said sleeve, said distal slots dividing said sleeve into a number of distal legs, said outwardly extending portion of said sleeve forming a toot adjacent a distal end of a respective one of said legs, said legs being moveable toward one another to grip said proximal portion of said implant therebetween, wherein in said second configuration said ring engages said feet and moves said legs toward one another to grip said proximal portion of said implant in said sleeve;

a clamp pivotally received in said receptacle of said connecting portion when said connecting portion is in a first configuration, wherein said elongate member extends through said clamp;

a sleeve positioned about said proximal portion of said implant, wherein said sleeve and said proximal portion are received in said aligned slots of said arms in the transverse orientation to the elongate member, said sleeve including an outwardly extending portion adjacent a distal end thereof;

a ring defining a bore that receives said sleeve so that said ring is positioned about said sleeve and in movable contact with said outwardly extending portion and a distal one of said pair of arms; and an engaging member engaged about said sleeve adjacent a proximal end thereof, said engaging member being threadingly movable along said sleeve to a second configuration where said engaging member contacts a proximal one of said pair of arms to compress said pair of arms against said ring and move said ring into contact with said outwardly extending portion of said sleeve to clamp said sleeve about said proximal portion of said implant.

7. The system of claim 6, wherein in said second configuration said connecting portion engages said clamp to lock said clamp in position therein.

8. The system of claim 7, wherein in said second configuration said clamp clampingly engages said elongate member.

9. The system of claim 8, wherein said clamp includes a passage through which said elongate member extends, said passage including a concave portion spaced from said elongate member in said second configuration, said concave portion extending between end portions clampingly engaging said elongate member in said second configuration.

10. The system of claim 8, wherein said implant s a bone screw with a threaded shaft distal of said proximal portion.

11. The system of claim 8, wherein said elongated slots include a length that extends transversely to the elongate member and transversely to the implant so that a distance between said elongate member and said implant can be varied by varying a position of said proximal portion of said implant along said length of said slots.

12. The system of claim 8, wherein said arms each include a facing surface, said facing surfaces facing one another in an angular orientation diverging away from said connecting portion in said first configuration and said facing surfaces are parallel to one another in said second configuration.

13. A method for coupling an elongate member to an implant engageable to a spinal column, comprising:

providing a coupler having a connecting portion defining a receptacle for receiving the elongate member therethrough and a pair of arms secured to one another with the connecting portion, the pair of arms defining elongated slots aligned with one another and extending transversely to the receptacle;

positioning the elongate member through the receptacle of the coupler, the receptacle including a clamp about the elongate member pivotally received in the receptacle;

positioning a proximal portion of the implant through the aligned slots, the proximal portion of the implant including a sleeve positioned thereabout and the sleeve extends through a ring that is in abutting engagement with the sleeve adjacent a distal end of the sleeve and an engaging member positioned about a proximal end of the sleeve, wherein the sleeve includes a number of proximal slots extending therethrough and opening at the proximal end of the sleeve to divide a proximal portion of the sleeve into a number of threaded fingers moveable toward one another into an aperture that extends through the proximal and distal ends of the sleeve and the aperture receives the proximal portion of the implant therein, the sleeve also including a number of distal slots extending therethrough along a distal portion of the sleeve and opening at the distal end of the sleeve, the distal slots dividing the distal portion of the sleeve into a number of legs moveable toward one another into the aperture of the sleeve; and moving the pair of arms toward one another to clamp the elongate member in the receptacle and to clamp the sleeve to the proximal portion of the implant by clamping the pair of arms between the engaging member and the ring and by clamping the fingers of the sleeve and the number of legs of the sleeve to the proximal portion of the implant.

14. The method of claim 13, wherein moving the pair of arms toward one another includes moving the arms from a first orientation where facing surfaces of the pair of arms diverge relative to one another away from the receptacle to a second orientation where the facing surfaces of the pair of anus are parallel to one another.

15. The method of claim 13, wherein moving the pair of arms toward one another includes threadingly advancing the engaging member along the sleeve into contact with the proximal one of the pair of arms and seating a distal one of the pair of arms against the ring that engages an outwardly extending portion of the sleeve.

16. The method of claim 13, wherein:
positioning the elongate member through the receptacle of the coupler includes pivoting the clamp in the receptacle to adjust an orientation of the coupler relative to the elongate member; and
positioning the proximal portion of the implant through the aligned slots includes adjusting a position of the coupler relative to the implant by moving the arms along the aligned slots relative to the proximal portion of the implant.

* * * * *